United States Patent [19]
Charles et al.

[11] Patent Number: 5,464,025
[45] Date of Patent: Nov. 7, 1995

[54] SELF-CONTAINED SURGICAL TUBING MANAGEMENT SYSTEM

[76] Inventors: Steven T. Charles, 3220 Oak Manor, Germantown, Tenn. 38138; John A. Ripley, 1233 Devon La., Newport Beach, Calif. 92660; John C. Huculak, 29125 Abotsinch, Laguna Niguel, Calif. 92677

[21] Appl. No.: 395,403

[22] Filed: Feb. 27, 1995

[51] Int. Cl.$^6$ ............................................ A61B 19/00
[52] U.S. Cl. ............................................ 128/849; 128/852
[58] Field of Search ............................ 128/849–856

[56] References Cited

U.S. PATENT DOCUMENTS

| | | | |
|---|---|---|---|
| 4,476,860 | 10/1984 | Collins | 128/852 |
| 4,553,538 | 11/1985 | Rafelson | 128/852 |
| 4,611,592 | 9/1986 | Talboy | 128/852 |
| 4,664,103 | 5/1987 | Martin | 128/852 |
| 5,010,899 | 4/1991 | Thompson | 128/852 |

*Primary Examiner*—Michael A. Brown
*Attorney, Agent, or Firm*—Jeffrey S. Schira

[57] ABSTRACT

A self-contained surgical tubing management system whereby all of the required surgical handpiece(s) and power and fluid tubings, cables and connections are incorporated in a single disposable package. The tubing management system includes a sterile sheet or substrate that may cover either all or only a portion of the patient's body. Pockets may be formed in either end of the sheet to hold, at one end, any number or variety of surgical instruments, such as vitreous probes, infusion cannulas, aspiration lines, coagulating probes, etc., and, at the end opposite the instruments, a small coils of power and fluid lines. The various power and fluid lines needed to operated these instruments may be permanently or temporarily connected to the respective instruments and extend down the length of the sheet. These lines are attached to the sheet either continuously or at various points by any number of methods.

33 Claims, 3 Drawing Sheets

SELF-CONTAINED SURGICAL TUBING MANAGEMENT SYSTEM

BACKGROUND OF THE INVENTION

Microsurgical instruments typically are used by surgeons for removal of tissue from delicate and restricted spaces in the human body, particularly in surgery on the eye, and more particularly in procedures for removal of the vitreous body or the crystalline lens. Such instruments include a control console and a surgical handpiece with which the surgeon dissects and removes the tissue. The handpiece has a surgical tool such as a pneumatic vitreous probe or an ultrasonic microsurgical cutter for cutting or fragmenting the tissue and is connected to the control console by a long air pressure (pneumatic) line or power cable and by long conduits, cable, optical cable or flexible tubes for supplying an infusion fluid to the surgical site and for withdrawing or aspirating fluid and cut/fragmented tissue from the site. The cutting, infusion and aspiration functions of the handpiece are controlled by the remote control console that not only provides power for the surgical handpiece(s) (e.g., a reciprocating or rotating cutting blade or an ultrasonically vibrated needle), but also controls the flow of infusion fluid and provides a source of reduced pressure (relative to atmosphere) for the aspiration of fluid and cut/fragmented tissue. The functions of the console are controlled manually by the surgeon, usually by means of a foot-operated switch.

The multiple connections that are required between the handpiece and the console for the power cable and the infusion and aspiration lines have made the preparation and interconnection of the equipment prior to the surgical procedure extremely complex, with the resultant concerns over maintaining the sterility of the equipment and assuring error-free connection. Accordingly, the typical microsurgical instruments, the fluid handling connections have come to be centralized in a "cassette" that contains in one unit the connections for the aspiration lines, internal conduits for directing the flow of fluids, valves for controlling the flow of fluids from the handpiece, a receptacle for aspirated fluid and tissue and may contain the tube portion of a peristaltic pump. The cassette typically is supplied in a sterile package with color-coded connecting tubing that may or may not be already attached. Nevertheless, setting up the equipment still requires connection of the cassette and console to handpiece infusion lines, handpiece aspiration lines, electrical power cables, pneumatic lines and/or fiberoptic cables and inserting the cassette into a receptacle in the console. In addition, several handpieces may be used during a typical operation, multiplying the number of lines that must be connected between the handpieces and the console. While color coding of the lines reduces the chances of misconnecting the lines, these multiple lines may become tangled and kinked easily as the console is generally outside of the sterile field and hence, several feet away from the operative site, thereby requiring the lines to be several feet long. Therefore, it is important that these lines remain stretched out and relatively straight in order to ensure that air and infusion/aspiration fluid flows freely to and from the operative site. Also, these lines may be connected to valves and/or stopcocks. Keeping the lines straight and untangled helps in associating the proper valve with the proper line.

Prior art devices, including the surgical drapes disclosed in U.S. Pat. Nos. 3,721,234 and 5,010,899 include integral tabs or loops into which the surgical lines may be placed and held during surgery. However, these drapes, while providing a means to hold the lines in place during surgery, do not address the problem of minimizing tangling and kinking of the lines prior to surgery, and reducing the likelihood of misconnected lines.

Accordingly, a need continues to exist for a self-contained surgical tubing management system that holds the various power and fluid lines used during surgery relatively straight, spaced apart from each other and pre-connected, thereby providing a complete tubing and cable package that more easily and reliably allows the surgical handpiece(s) to be connected to a surgical console.

BRIEF SUMMARY OF THE INVENTION

The present invention is intended to improve upon the prior art by providing a self-contained surgical drape whereby the most commonly used surgical handpiece(s) and power and fluid tubings, cables and connections are pre-connected incorporated in a single disposable package. The drape portion of the present invention generally includes a sterile sheet or substrate that may cover either all or only a portion of the patient's body. Pockets may be formed in either end of the sheet. Into the pocket intended to be placed next to the patient's head any number or variety of surgical instruments, such a vitreous probes, infusion cannulas, aspiration lines, coagulating probes, etc., may be placed. The various power and fluid lines needed to operate these instruments may be permanently or temporarily connected to the respective instruments and extend down the length of the sheet. These lines are attached to the sheet at various points by any number of methods, such as adhesive, adhesive tape, hook and loop fasteners or by threading the lines through slits made in the sheet. Alternatively, the sheet may be of a two-ply construction with the lines sandwiched between the plies. These lines terminate in the pocket opposite the instrument pocket. This second pocket contains a small spool of each lines so that the lines can be extended beyond the outline of the sheet and connected to the surgical console.

Accordingly, one objective of the present invention is to provide a self-contained surgical tubing management system wherein the various lines are pre-attached to the surgical drape or sheet and are removable, replaceable and can be supplemented with additional attached lines.

Another objective of the present invention is to provide a self-contained surgical tubing management system wherein the various lines are spaced apart from each other.

Still another objective of the present invention is to provide a self-contained surgical tubing management system wherein the most commonly used instruments for surgery are preassembled and contained within a sheet.

Another objective of the present invention is to prove a self-contained surgical tubing management system wherein the most commonly used instruments for surgery are easily located near the surgeon and connected to a surgical console.

Another objective of the invention is to provide a self-contained surgical tubing management system that is easily unfolded in place on the patient.

Still another objective of the present invention is to provide a self-contained surgical tubing management system that minimizes tangling and kinking of the various power and fluid lines needed to operate a surgical instrument.

Still another objective of the present invention is to provide a self-contained surgical tubing management system that minimizes the likelihood of misconnecting the various power and fluid lines needed to operate a surgical instrument.

Additional objectives and advantages of the present invention will become apparent to those skilled in the art from the detailed description and drawings that follow.

DETAILED DESCRIPTION OF THE INVENTION

Figure 1:
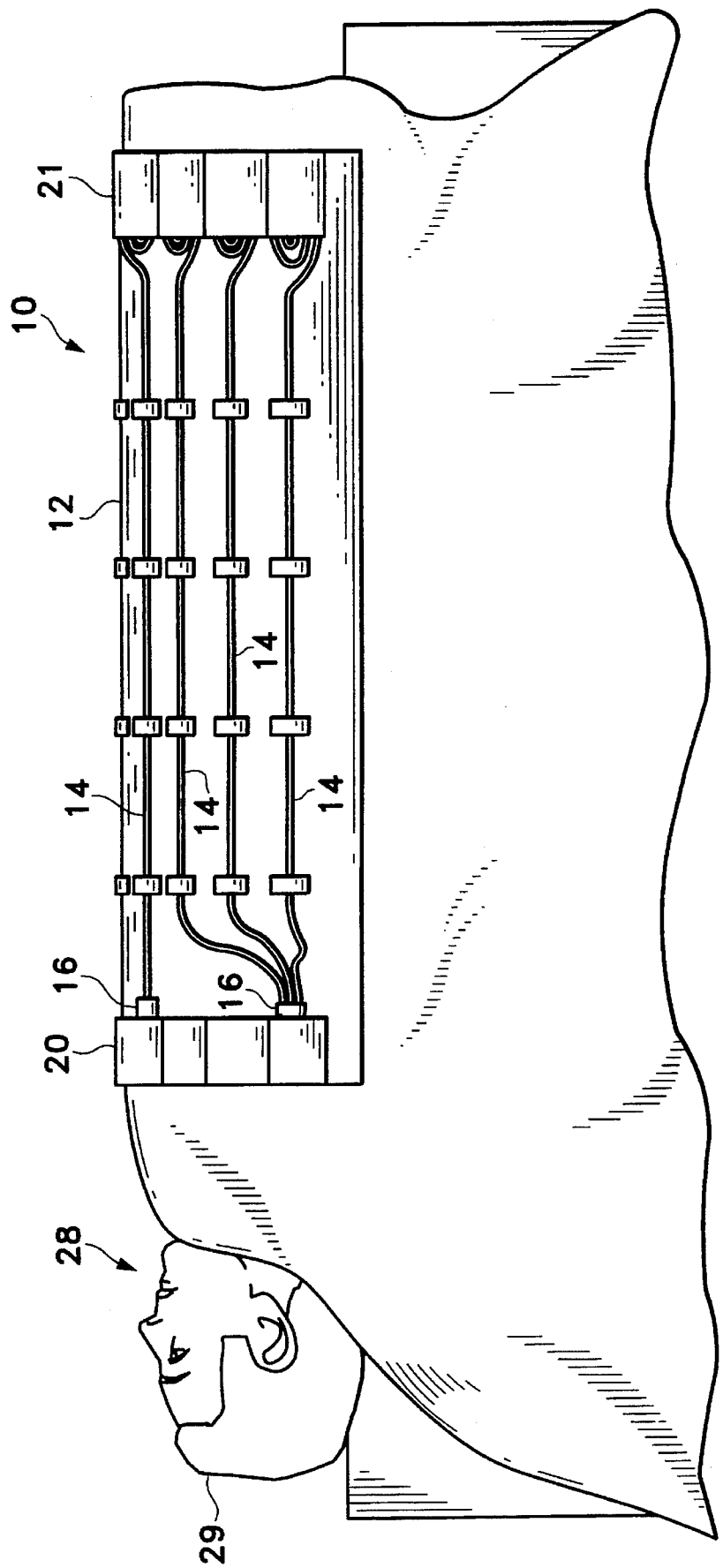
FIG. 1 is an elevational view of a first embodiment of the present invention placed on a patient.
Figure 2:
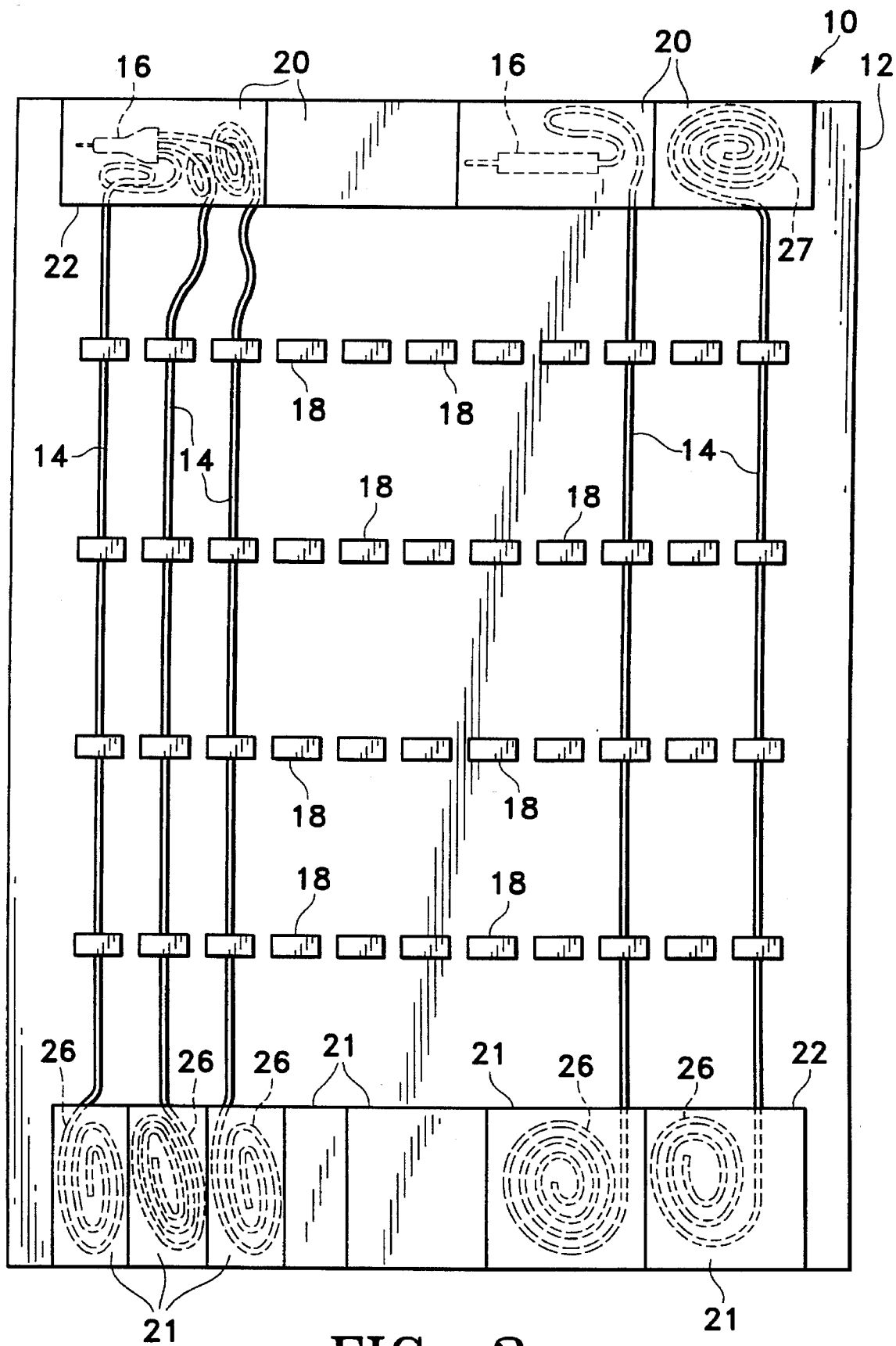
FIG. 2 is a plan view of the first embodiment of the present invention illustrated in FIG. 1.
Figure 3:
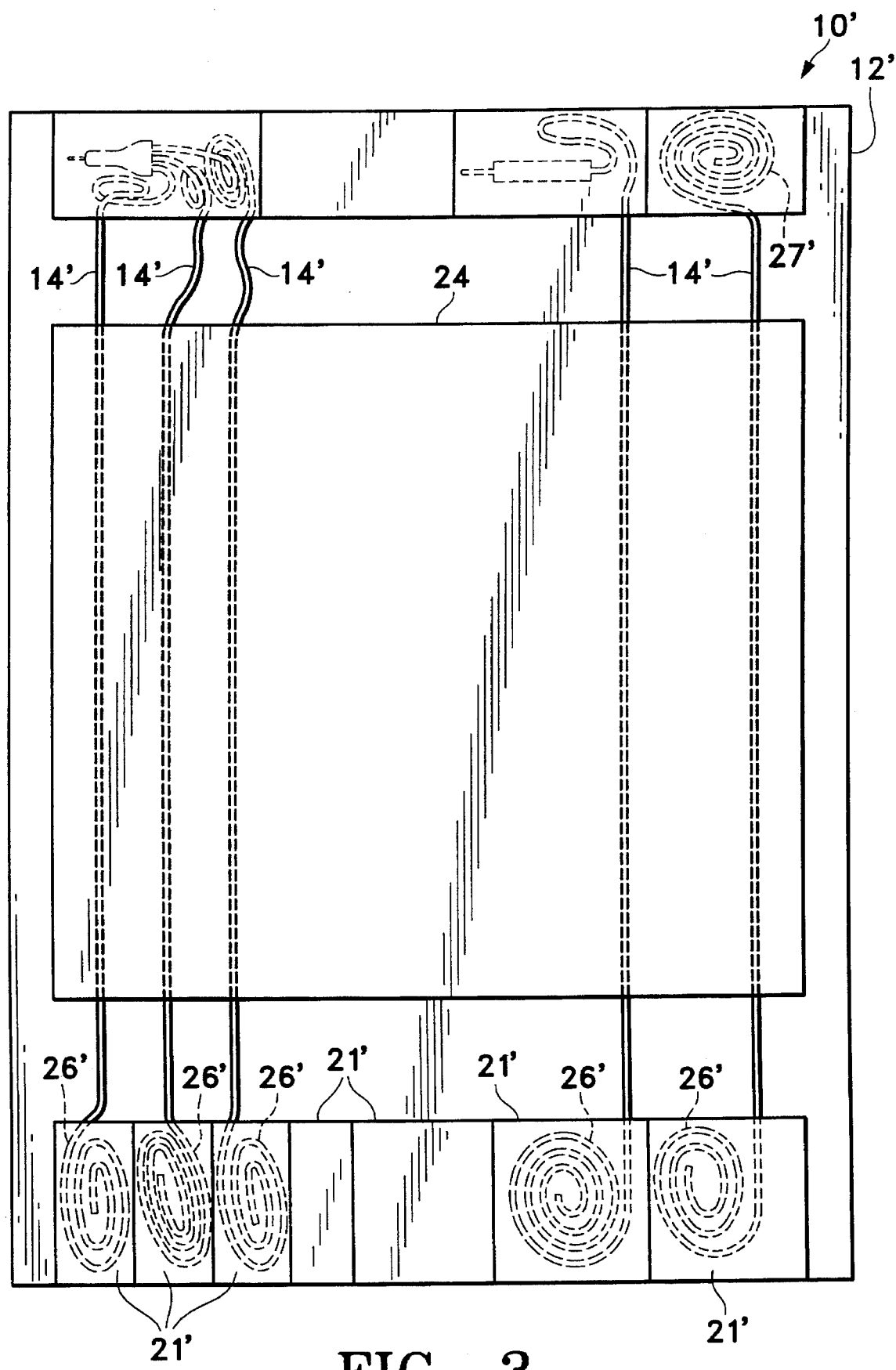
FIG. 3 is a plan view of a second embodiment of the present invention.

As can best be seen in FIGS. 1 and 2, the self-contained surgical tubing management system 10 of the present invention generally consists of substrate or drape 12, lines 14 and surgical instruments 16. Instruments 16 may be any of a variety of surgical devices, such as a vitreous probe, a phacoemulsification or fragmentation handpiece, a coagulating probe, a laser probe, an infusion cannula, an aspiration line, a fiber optic illuminator probe or any other probe used by a surgeon and/or assistant that connects to the supporting console/device. Lines 14 may be any of a variety of fluid, optical or power (electrical, pneumatic or light/laser) lines necessary for operating instruments 16. Lines 14 usually will be electrical cables, flexible fluid tubings or fiber optic cables, although any type of line 14 may be used, these cables and tubings being well-known in the art. Preferably, lines 14 are colored coded for the particular instrument 16 to which lines 14 are connected and may be permanently attached to instruments 16 or, as illustrated in FIG. 2, lines 14 may be left unconnected to any instrument 16 and may terminate in a coil 27 that may be used as a spare line 14. Lines 14 terminate at free ends containing connectors (not shown) such as luer lock, CPC, Lemo or fiberoptic connectors. Preferably the connector used for each line 14 is of a unique type, thereby minimizing the likelihood of misconnecting the lines 14 to the surgical console (not shown). As can be seen in FIGS. 2 and 3, lines 14 are longer than substrate 12 so that lines 14 can be extended beyond the limits of substrate 12 and connected to the control console (not shown) and so that instruments 16 can be extended beyond the limits of substrate 12.

Substrate 12 may be any of a variety of cloth, plastic, non-woven fabric (such as non-woven polypropylene) or paper materials commonly used in an operating room as a drape material. Substrate 12 preferably should be a material that can be folded and sterilized and may be either relatively small (so as not to cover the entire patient) as shown in FIG. 1, or may be large enough to cover the entire patient. As best seen in FIG. 2, substrate 12 contains a plurality of fasteners 18 for attaching lines 14 to substrate 12. Fasteners 18 may be any of a variety of commonly available fasteners such as hook and loop fasteners (such as those sold under the trademark VELCRO®), snap fasteners, adhesive tape, twist ties, snap-in fastener or cable ties or fasteners 18 may consist of a plurality of loop forming slits cut into substrate 12 with lines 14 threaded through the slits to hold lines 14 to substrate 12. Alternatively, as shown in FIG. 3, lines 14' are held against substrate 12 by sheet 24 that is adhered or woven to substrate 12', sandwiching lines 14' between sheet 24 and substrate 12'. Substrate 12 may also contain a plurality of pockets 20 and 21 made by either attaching a second piece of material 22 (such as clear plastic) at either end of substrate 12 or by folding over the ends of substrate 12. Pockets 20 and 21 may be used to hold surgical instruments 16 or coiled ends 26 of lines 14.

During manufacture of system 10, a portion of the end of lines 14 opposite instruments 16 is formed into coils 26 and placed in pockets 21. Lines 14 and instruments 16 are extended down the length of substrate 12, with lines 14 and instruments 16 either being threaded through fasteners 18 or fasteners 18 being applied over lines 14. Instruments 16 are placed in pockets 20 along with a small coil of respective line 14 (so that instruments 16 can be extended into the operative site). Substrate 12 is then rolled or folded into a compact package. As best illustrated in FIG. 1, in use, rolled or folded tubing management system 10 is placed on supine patient 28 and unrolled or unfolded so that pockets 20 containing instruments 16 are located near head 29 of patient 28 and pockets 21 containing coils 26 of lines 14 are located at the feet (not shown) of patient 28. The surgical console (not shown) may be placed at the feet or beside patient 28. Coils 26 are removed from pockets 21 and uncoiled so that lines 14 may be easily connected to the console. Instruments 16 may be removed from pockets 20 and placed near the operative site prior to the beginning of surgery or may be left in pockets 20 until required by the surgeon. As can be seen, the use of lines 14 attached to substrate 12 by fasteners 18 substantially eliminates the likelihood that lines 14 may become entangled or kinked, thereby reducing the possibility of misconnecting of lines 14 and reducing the amount of time required to connect instruments 16 to the console. In addition, other loose articles that may be required during surgery, such as the cassette (not shown), knives (not shown), gauze (not shown), eye spears (not shown) or other surgical devices may be wrapped conveniently within rolled or folded tubing management system 10 or placed in spare pockets 20 or 21 for delivery to the operating suite.

The invention having now been fully described, it should be understood that it may be embodied in other specific forms or variations without departing from its spirit or essential characteristics. Accordingly, the embodiments described above are to be considered in all respects as illustrative and not restrictive.

We claim:

1. A self-contained surgical tubing management system, comprising:

a) a substrate having a length;

b) at least one surgical instrument retained on the substrate at an end of the substrate placed near a head of a patient;

c) at least one line connected on one end to the surgical instrument, extending down the length of the substrate and terminating at a free end opposite the surgical instrument; and d) a means for attaching the line to the substrate.

2. The surgical tubing management system of claim 1 wherein the substrate is a surgical drape material and the means for attaching the line to the substrate comprises a plurality of loop forming slits cut into the substrate.

3. The surgical tubing management system of claim 1 wherein the substrate is paper and the means for attaching the line to the substrate comprises a plurality of loop forming slits cut into the substrate.

4. The surgical tubing management system of claim 1 wherein the means for attaching the line to the substrate comprises a sheet placed over the line and adhered to the substrate.

5. The surgical tubing management system of claim 1 wherein the means for attaching the line to the substrate comprises adhesive tape.

6. The surgical tubing management system of claim 1 wherein the means for attaching the line to the substrate comprises hook and loop fasteners.

7. The surgical tubing management system of claim 1 wherein the substrate is cloth.

8. The surgical tubing management system of claim 1 wherein the substrate is non-woven polypropylene.

9. The surgical tubing management system of claim 1 wherein the line is a tubing.

10. The surgical tubing management system of claim 1 wherein the line is a power cable.

11. The surgical tubing management system of claim 1 wherein the line is a fiber optic cable.

12. The surgical tubing management system of claim 1 wherein the substrate covers substantially the entire patient.

13. A self-contained surgical tubing management system, comprising:

a) a substrate having a length;

b) a plurality of surgical instruments retained on the substrate at an end of the substrate placed near a head of a patient;

c) a plurality of lines, each line connected on one end to one of the surgical instruments, each line extending down the length of the substrate and terminating at a free end opposite the surgical instruments; and d) a means for attaching the lines to the substrate.

14. The surgical tubing management system of claim 13 wherein the substrate is surgical drape material and the means for attaching the lines to the substrate comprises a plurality of loop forming slits cut into the substrate.

15. The surgical tubing management system of claim 13 wherein the substrate is paper and the means for attaching the lines to the substrate comprises a plurality of loop forming slits cut into the substrate.

16. The surgical tubing management system of claim 13 wherein the means for attaching the lines to the substrate comprises a sheet placed over the lines and adhered to the substrate.

17. The surgical tubing management system of claim 13 wherein the means for attaching the lines to the substrate comprises adhesive tape.

18. The surgical tubing management system of claim 13 wherein the means for attaching the lines to the substrate comprises hook and loop fasteners.

19. The surgical tubing management system of claim 13 wherein the substrate is cloth.

20. The surgical tubing management system of claim 13 wherein the substrate is non-woven polypropylene.

21. The surgical tubing management system of claim 13 wherein the lines are tubing.

22. The surgical tubing management system of claim 13 wherein the substrate covers substantially the entire patient.

23. A self-contained surgical tubing management system, comprising:

a) a surgical drape material substrate having a length;

b) a plurality of surgical instruments retained on the substrate at an end of the substrate placed near a head of a patient;

c) a plurality of fluid tubings, each tubing connected on one end to one of the surgical instruments, each tubing extending down the length of the substrate and terminating at a free end opposite the surgical instruments;

d) at least one power cable connected to one of the surgical instruments, the cable extending down the length of the substrate and terminating at a free end opposite the surgical instrument; and e) a means for attaching the fluid tubings and the power cable to the substrate.

24. The surgical tubing management system of claim 23 wherein the means for attaching the fluid tubings and the power cable to the substrate comprises a plurality of loop forming slits cut into the substrate.

25. The surgical tubing management system of claim 23 wherein the means for attaching the fluid tubings and the power cable to the substrate comprises a sheet placed over the line and adhered to the substrate.

26. The surgical tubing management system of claim 23 wherein the means for attaching the fluid tubings and the power cable to the substrate comprises adhesive tape.

27. The surgical tubing management system of claim 23 wherein the means for attaching the fluid tubings and the power cable to the substrate comprises hook and loop fasteners.

28. A self-contained surgical tubing management system, comprising:

a) a non-woven polypropylene substrate having a length;

b) a plurality of surgical instruments retained on the substrate at an end of the substrate placed near a head of a patient;

c) a plurality of fluid tubings, each tubing connected on one end to one of the surgical instruments, each tubing extending down the length of the substrate and terminating at a free end opposite the surgical instruments;

d) at least one power cable connected to one of the surgical instruments, the cable extending down the length of the substrate and terminating at a free end opposite the surgical instrument; and e) a means for attaching the fluid tubings and the power cable to the substrate.

29. The surgical tubing management system of claim 28 wherein the means for attaching the fluid tubings and the power cable to the substrate comprises a plurality of loop forming slits cut into the substrate.

30. The surgical tubing management system of claim 28 wherein the means for attaching the fluid tubings and the power cable to the substrate comprises a sheet placed over the line and adhered to the substrate.

31. The surgical tubing management system of claim 28 wherein the means for attaching the fluid tubings and the power cable to the substrate comprises adhesive tape.

32. The surgical tubing management system of claim 28 wherein the means for attaching the fluid tubings and the power cable to the substrate comprises hook and loop fasteners.

33. The surgical tubing management system of claim 28 wherein the surgical instruments are retained within pockets formed on the substrate.

* * * * *